United States Patent [19]

Koppel et al.

[11] Patent Number: 5,358,720
[45] Date of Patent: Oct. 25, 1994

[54] TREATMENT OF ARTHRITIC CONDITIONS

[76] Inventors: Richard M. Koppel, 554 River Vale Rd.; Karl Verebey, 638 Debchar Ct., both of River Vale, N.J. 07675

[21] Appl. No.: 139,742

[22] Filed: Oct. 22, 1993

[51] Int. Cl.⁵ ............... A61K 33/32; A61K 35/78; A61K 33/26; A61K 31/70

[52] U.S. Cl. .................. 424/639; 424/195.1; 424/641; 424/646; 514/52; 514/168; 514/356; 514/474; 514/492; 514/494; 514/825; 514/905

[58] Field of Search .......... 514/356, 474, 825, 168, 514/52, 905, 492, 494; 424/195.1, 639, 641, 646

[56] References Cited

U.S. PATENT DOCUMENTS

| | | | |
|---|---|---|---|
| 4,252,797 | 2/1981 | Rosenthal | 424/201 |
| 4,619,829 | 10/1986 | Motschan | 424/128 |
| 4,647,453 | 3/1987 | Meisner | 424/54 |
| 4,968,510 | 11/1990 | Jensen | 424/630 |

*Primary Examiner*—Raymond J. Henlely, III
*Attorney, Agent, or Firm*—Richard C. Litman

[57] ABSTRACT

A regimented therapeutic method for he alleviation of arthritic conditions by orally administering a selective combination of vitamins and minerals in scheduled dosage amounts. The daily scheduled regiment involves the administration of about 25–100 mg of nicotinic acid three times per day, about 200–1000 mg of calcium ascorbate three times a day, and a single dosage form of a copper-free multivitamin with multiminerals to be taken once a day.

9 Claims, No Drawings

TREATMENT OF ARTHRITIC CONDITIONS

BACKGROUND OF THE INVENTION

1. Field of the Invention

The present invention relates to the utilization of nutritional supplements in the treatment of certain inflammatory disorders. More particularly, this invention pertains to a regimented therapeutic method for the alleviation of arthritic conditions by orally administering a selective combination of vitamins and minerals in scheduled dosage amounts.

2. Description of the Prior Art

Current medical treatment of arthritis is largely limited to the use of steroidal or non-steroidal antiflammatory/analgesic drugs. However, these pharmaceutical agents present toxicity problems with frequent administration and their use must be carefully monitored to avoid adverse side effects. Even moderate administrations of such synthetic steroids as cortisone, prednisone and dexamethasone may adversely effect protein metabolism of the bones, which can lead to calcium depletion.

To obviate the deleterious effects of calcium loss resulting from the use of conventional steroids, U.S. Pat. No. 4,252,797 to Rosenthal suggests the simultaneous administration of an anti-inflammatory preparation containing a corticosteriod and calcium compounds for treatment of arthritis and other rheumatic diseases. The preferred calcium compounds include calcium salts of organic acids. This patent further discloses the optional addition of vitamins $B_{12}$, C and/or D to the anti-inflammatory preparation to facilitate calcium absorption.

The use of relatively mild anti-inflammatory agents such as sugars and amino acids for the treatment of degenerative join diseases is taught in U.S. Pat. No. 4,647,453 to Meisner. This treatment method also includes the oral administration of ascorbic acid and biologically available calcium, in combination with other natural substances to particularly treat osteoarthritis.

U.S. Pat. No. 4,619,829 to Motschan generally discloses the use of a single or a combination of various vitamins in the long-term treatment or prevention of rheumatic diseases. The preferred vitamin or combination of vitamins is disclosed as belonging to the vitamin-B-complex, which may be supplemented with minerals and/or trace elements.

The treatment of arthritis and bursitis through the use of an orally ingested mixture of mineral compounds is described in U.S. Pat. No. 4,968,510 to Jensen. The essential components of the disclosed mixture include oxides of aluminum and magnesium in combination with iron and minor amounts of silicon, sodium and potassium, together with trace amounts of such elements as calcium, zinc and copper.

From the foregoing, it is apparent that here remains an important need in the prior art for a therapeutic method to treat arthritic disorders which not only utilizes selective nutritional substances, but provides for the regimented administration of these substances in convenient dosage forms.

SUMMARY OF THE INVENTION

It is, accordingly, a primary object of the present invention to provide for the utilization of selective nutritional supplements in the treatment of arthritic conditions.

It is another object of the invention to provide a therapeutic regiment for alleviating the effects of arthritis by conveniently administering the active nutritional substances in scheduled dosage amounts.

It is a further object of the invention to provide method of effectively treating arthritis on a continuous or long-term basis without adverse side effects.

These and other objects are accomplished in accordance with the present invention which provides a method for the treatment of arthritic conditions which comprises the oral administration of a combination of nutritional substances consisting essentially of about 25-100 mg of nicotinic acid administered three times per day, about 200-1000 mg of calcium ascorbate administered three times a day, and a single dosage form of a copper-free multivitamin with multiminerals to be taken once a day. Each of the present substances can be individually formulated into dosage forms, with an initial dose including separate measured amounts of the three therapeutic substances. Long-term utilization of the combination of substances in conformance with the present method facilitates a noticeable increase in mobility of the joints and results in a significant reduction of the levels of reported pain in arthritic sufferers.

The therapeutic effectiveness of the present method depends not only on the selective anti-arthritic activity of the combination of nutritional supplements utilized, but also on the patient's adherence to the daily regiment and timely administration of these active substances on a long-term basis.

The forgoing and other features, advantages and objects of the invention may be more fully appreciated by reference to the following detailed description.

DETAILED DESCRIPTION OF THE PREFERRED EMBODIMENTS

In accordance with the present invention, the nicotinic acid (also called niacin) may be formulated as tablets, capsules or powder preparations, each having a measured unit of administration of about 25-100 mg. Preferably, the nicotinic acid is limited to about 100 mg per dosage since oral administration of this odorless, crystalline compound in amounts substantially greater than 100 mg per dose can result in a physiological reaction referred to as the "niacin flush". This reaction is believed to be caused by the vasodilator and histamine-releasing effects of nicotinic acid, and is generally experienced as tingling or itching sensation, which may be accompanied by reddening in of the face and other parts of the body. These symptoms may persist for 20-30 minutes, but usually diminish and completely disappear with continued administration of niacin at dosage levels of 100 mg, taken three times per day at morning, noon and evening. While individual sensitivity to niacin varies, it may be may be advisable for certain hypersensitive patients to use $\frac{1}{2}$ or $\frac{1}{4}$ of a scored 100 mg niacin tablet for at least one week at the beginning of the present therapy. Thereafter, if no significant discomfort or flushing is observed. nicotinic acid may be continued at the preferred maintenance dose of 100—mg three times/day indefinitely.

While it has been previously established that nicotinic acid is an important biochemical component of such cellular reactions as nicotine adenosine dinucleotide (NAD) and nicotine adenosine dinucleotide phosphate (NADP), it is not understood at this time which underlying biochemical action is responsible for the antiarthritic effectiveness of this substance when utilized in accordance with the present regiment. It is believed, however, that niacin's histamine-releasing properties and ability to increase blood flow play a critical role in its therapeutic effectiveness. Moreover, it has been discovered that similar B-complex vitamins such as niacinamide are not chemically equivalent in effectiveness to niacin when used in the treatment of arthritis according to the present invention. In this regard it is noted that niacinamide does not dilate blood vessels nor does it release histamine within the body.

Another significant substance employed in the present method is calcium ascorbate, a buffered form of vitamin C. Tablets and/or capsules of calcium ascorbate are generally administered three times a day at morning, noon and evening in dosage forms of 200–1000 mg. Preferable, a 500 mg dosage of calcium ascorbate is taken by an arthritic sufferer in accordance with the present daily regiment. This particular substance is preferred over ascorbic acid because the buffering effect of calcium does not cause abdominal distress. Again, the exact mechanism of biological action which accounts for alleviation of arthritic induced pain and inflammation when calcium ascorbate is used in combination with the other substances of the present invention is not known. However, the role of this form of vitamin C in cellular regeneration, muscular tissue maintenance and tissue recovery acceleration is believed to account for its beneficial effects in controlling arthritic inflammation when utilized in conformance with the present therapy. It should be noted that vitamin C may precipitate a "gouty arthritic" attack. Therefore, patients with this condition should proceed with caution, preferably under the supervision of a physician, when practicing the present therapy.

The multivitamin-multiminerals supplement used in accordance with the present invention may be any such high-potency dietary formula which does not contain copper. Although copper is an essential trace metal and a co-factor in several enzymatic processes, the metal is so prevalent in many foods that additional supplementation is not recommended. This restriction is especially critical since excessive accumulation of copper in the joints of arthritic patients has been observed and is believed to one of the prime suspect trace metals in causing chronic joint diseases.

Suitable multiminerals for purposes of the present invention include iodine, calcium, potassium, iron, magnesium, manganese, zinc and selenium, preferably in the form of chelates. Of the preferred multivitamins, mention here is made of vitamins A, D, E, $B_1$, $B_2$, $B_6$, $B_{12}$, choline bitartrate, inositol, paba, pantothenic acid, biotin, rutin, betain, and glutamic acid. The copper-free multivitamin-multiminerals preparation utilized in the present regiment is preferably administered orally as a single tablet per day in the morning in combination with 100 mg of nicotinic acid and 500 mg of calcium ascorbate.

A preferred multivitamin-multimineral tablet for use in the present therapy contains the following ingredients:

| Ingredients | Amounts per Tablet |
| --- | --- |
| Vitamin A | 17,500 units |
| Vitamin D | 400 units |
| Vitamin E | 150 units |
| Vitamin $B_1$ | 75 mg |
| Vitamin $B_2$ | 75 mg |
| Vitamin C | 250 mg |
| Vitamin $B_6$ | 75 mg |
| Vitamin $B_{12}$ | 75 mcg |
| Niacinamide | 75 mg |
| Choline Bitartrate | 75 mg |
| Inositol | 75 mg |
| Paba | 75 mg |
| Pantothenic Acid | 75 mg |
| Biotin | 75 mcg |
| Folic Acid | 400 mcg |
| Rutin | 25 mg |
| Citrus Bioflavonoid | 25 mg |
| Hesperiden Complex | 5 mg |
| Betain HCl | 25 mg |
| Glutamic Acid | 25 mg |
| Iodine (kelp)* | 150 mcg |
| Calcium* | 50 mg |
| Potassium* | 10 mg |
| Iron* | 10 mg |
| Magnesium* | 7.20 mg |
| Manganese* | 6.10 mg |
| Zinc* | 15 mg |
| Selenium* | 10 mcg |

*mineral in the form of chelate

Another preferred multivitamin-multimineral tablet for in the present therapy contains the following ingredients:

| Ingredients | Amount per Tablet |
| --- | --- |
| Vitamin A | 17,500 units |
| Vitamin D | 400 units |
| Vitamin E | 150 units |
| Vitamin $B_1$ | 75 mg |
| Vitamin $B_2$ | 75 mg |
| Vitamin C | 250 mg |
| Vitamin $B_6$ | 75 mg |
| Vitamin $B_{12}$ | 75 mcg |
| Niacinamide | 75 mg |
| Choline Bitartrate | 75 mg |
| Inositol | 75 mg |
| Paba | 75 mg |
| Pantothenic Acid | 75 mg |
| Biotin | 75 mcg |
| Folic Acid | 400 mcg |
| Rutin | 25 mg |
| Citrus Bioflavonoid | 25 mg |
| Hesperiden Complex | 5 mg |
| Betain HCl | 25 mg |
| Glutamic Acid | 25 mg |
| Iodine | 150 mcg |
| Calcium | 50 mg |
| Potassium | 10 mg |
| Iron | 10 mg |
| Magnesium | 7.20 mg |
| Manganese | 6.10 mg |
| Zinc | 15 mg |
| Selenium | 10 mcg. |

The daily dose schedule of the present invention preferably includes the above copper-free multivitamin-multimineral tablet with the morning dose of 100 mg of nicotinic acid and 500 mg of calcium ascorbate; the noon and evening doses include only the nicotinic acid and calcium ascorbate. Although there is normally no adverse effects from taking these nutritional substances on an empty stomach, the scheduled doses are recommended to be taken with meals at breakfast, lunch and dinner, at least during the initial stages of the present therapy. Thereafter, as the patient becomes accustomed to the regiment, the substances may be taken at any time before or after a meal. When taken in this manner, the absorption of these therapeutic substances will be more complete since there in no immediate competition with food for abdominal absorption. As a dietary recommendation, such foods as meats, dairy products with saturated fats, and foods high in sugar should be consumed in limited quantities In order to facilitate an increase in the therapeutic effectiveness of the present method.

Utilization of the combination of nutritional substances in accordance with the invention described hereinabove, results in a significant reduction of pain and increase of joint mobility for most individuals in about four to six months. While the period for an effective therapeutic response varies with individuals, partial recovery or significant improvement has been observed in certain arthritic patients in as little as two months after starting the present therapy. An important prerequisite for a positive response is regular adherence to the present regiment for as long as it takes to achieve an improvement or complete recovery from the arthritic condition. This may take several months or years, and it may be particularly advantageous if the present treatment continues for life. The daily oral administration of the nutritional doses in conformance with the present invention can not only be of benefit in treating existing arthritis, but may serve as a preventative measure by retarding or eliminating the symptoms associated with early arthritic conditions.

The specific case studies described hereinafter serve to further illustrate the beneficial results of the present nutritional therapy. In all instances, 100 mg tablets of nicotinic acid, 500 mg tablets of calcium ascorbate, and a copper-free multivitamin-multimineral tablet having the formula specifically set forth hereinabove were orally administered according to the following daily schedule:

| DAILY DOSAGE SCHEDULE | | | |
| --- | --- | --- | --- |
| Substance | Breakfast | Lunch | Dinner |
| Nicotinic Acid | 100 mg | 100 mg | 100 mg |
| Calcium Ascorbate | 500 mg | 500 mg | 500 mg |
| Multivitamin-multimineral | 1 tablet | — | — |

CASE A

A 62 year old male patient was suffering from inflamed arthritic knees, which required surgery. Patient was daily taking aspirin, ibuprofen, and various other drugs for pain. He began taking the above nutritional substances in conformance with the above schedule and within six months was reported free of pain, without any harmful side effects.

CASE B

A 75 year old female patient had arthritis in the lower spine and hips. Patient described physician's diagnosis as degenerative arthritis and osteoporosis. Within about four months after regularly taking the above substances, she experienced less pain, and two months later the pain was completely gone.

CASE C

A 47 year old male with arthritis in both knees and several fingers began the present therapy according to the daily schedule described above. In about three month, he experienced pain relief and increased mobility.

CASE D

A male, age 84, with arthritis in his leg and hip began the present daily therapy in December of 1992. First signs of pain relief and increased mobility occurred in March of 1993. Prior to instant therapy, patient took ibuprofen daily with poor results.

CASE E

A 67 year old male was suffering from severe arthritis in his left knee. The patient's knee was quite distorted and caused him to walk with an unusual gate. An artificial knee was recommended by his physician, but he declined this mode of remedy. After fourteen months of the present treatment described above, some relief and greater mobility was noticed.

CASE F

A female, age 75 with arthritis of hands, feet, ankle and knees suffered with pain and limited movement. Four month after the present regimen, patient reported a decrease in pain and greater mobility. After almost 2 years of the present nutritional treatment, she reported no pain, no swelling and greater mobility.

It should be understood that there may be various changes and modifications of the representative embodiments herein selected for purposes of illustration without departing from the spirit and scope of the invention. Accordingly, the foregoing embodiments art not to be interpreted as restrictive of the invention beyond that necessitated by the following claims.

We claim:

1. A method for the treatment of arthritic conditions amenable to the treatment which comprises orally administering to a host in need thereof a combination of nutritional substances consisting essentially of about 25–100 mg of nicotinic acid administered three times per day, about 200–1000 mg of calcium ascorbate administered three times a day, and a single dosage form of a copper-free multivitamin with multiminerals also to be taken once a day.

2. The method according to claim 1 wherein the nutritional substances are each formulated into individual dosage forms 3. The method according to claim 2 wherein the nutritional substances consists essentially of a 100 mg tablet of nicotinic acid, a 500 mg tablet of calcium ascorbate, and a tablet of the copper-free multivitamin with multiminerals.

4. The method according to claim 1 wherein the multivitamin is a mixture of vitamins A, D, E, $B_1$, $B_2$, $B_6$, $B_{12}$, choline bitartrate, inositol, paba, pantothenic acid, biotin, rutin, betain, and glutamic acid.

5. The method according to claim 1 wherein the multiminerals are a mixture of iodine, calcium, potassium, iron, magnesium, manganese, zinc and selenium in the form of chelates.

6. The method according to claim 1 wherein the nicotinic acid and calcium ascorbate are daily administered in the morning, noon and evening.

7. The method according to claim 6 wherein the single dosage of the copper-free multivitamin with multiminerals is daily administered in the morning.

8. The method according to claim 6 wherein the nicotinic acid and calcium ascorbate are administered before or after breakfast, lunch and dinner.

9. The method according to claim 1 wherein he single dosage form of a copper-free multivitamin with multiminerals is a tablet containing the following ingredients in the following designated amounts:

| | |
|---|---|
| Vitamin A | 17,500 units |
| Vitamin D | 400 units |
| Vitamin E | 150 units |
| Vitamin $B_1$ | 75 mg |
| Vitamin $B_2$ | 75 mg |
| Vitamin C | 250 mg |
| Vitamin $B_6$ | 75 mg |
| Vitamin $B_{12}$ | 75 mcg |
| Niacinamide | 75 mg |
| Choline Bitartrate | 75 mg |
| Inositol | 75 mg |
| Paba | 75 mg |
| Pantothenic Acid | 75 mg |
| *-continued* | |
| Biotin | 75 mcg |
| Folic Acid | 400 mcg |
| Rutin | 25 mg |
| Citrus Bioflavonoid | 25 mg |
| Hesperiden Complex | 5 mg |
| Betain HCl | 25 mg |
| Glutamic Acid | 25 mg |
| Iodine | 150 mcg |
| Calcium | 50 mg |
| Potassium | 10 mg |
| Iron | 10 mg |
| Magnesium | 7.20 mg |
| Manganese | 6.10 mg |
| Zinc | 15 mg |
| Selenium | 10 mcg. |

\* \* \* \* \*